United States Patent
Berg

(10) Patent No.: US 6,403,642 B1
(45) Date of Patent: Jun. 11, 2002

(54) SULFUR ADSORBENT FOR REDUCING ONION OR GARLIC BREATH ODOR

(75) Inventor: Kenneth A. Berg, North Wales, PA (US)

(73) Assignee: PQ Holding, Inc., Wilmington, DE (US)

(*) Notice: Subject to any disclaimer, the term of this patent is extended or adjusted under 35 U.S.C. 154(b) by 0 days.

(21) Appl. No.: 09/638,837

(22) Filed: Aug. 14, 2000

Related U.S. Application Data

(60) Provisional application No. 60/149,031, filed on Aug. 16, 1999.

(51) Int. Cl.[7] .................. A61K 31/195; A61K 31/30; A61K 31/695; A61K 33/34; A61K 9/68
(52) U.S. Cl. .................. 514/499; 424/48; 424/49; 424/54; 514/562; 514/770
(58) Field of Search .............. 424/48–58, 484, 424/954; 514/499, 562, 770

(56) References Cited

U.S. PATENT DOCUMENTS

| | | | |
|---|---|---|---|
| 3,070,508 A | | 12/1962 | Siegel et al. |
| 3,888,976 A | * | 6/1975 | Mlkvy et al. .................. 417/44 |
| 4,153,680 A | * | 5/1979 | Seybert ........................ 424/49 |
| 4,303,641 A | * | 12/1981 | Dewolf et al. ................. 424/49 |
| 4,352,828 A | * | 10/1982 | Rialland et al. ............ 426/271 |
| 4,460,616 A | * | 7/1984 | Rialland et al. ............ 426/580 |
| 4,632,826 A | * | 12/1986 | Ploger et al. .................. 424/52 |
| 4,652,444 A | | 3/1987 | Maurer |
| 4,888,157 A | | 12/1989 | Carnell et al. |
| 4,952,392 A | | 8/1990 | Thame |
| 5,651,958 A | * | 7/1997 | Rice ............................. 424/49 |
| 5,817,294 A | * | 10/1998 | Arnold ........................ 424/44 |
| 5,882,631 A | * | 3/1999 | Suga et al. .................... 424/49 |
| 5,965,110 A | * | 10/1999 | Arnold ........................ 424/44 |
| 6,244,096 B1 | * | 6/2001 | Lewis et al. ................. 73/23.2 |

FOREIGN PATENT DOCUMENTS

| | | |
|---|---|---|
| JP | 6253769 | 9/1994 |
| JP | 9052833 | 2/1997 |
| WO | 86/00004 | 1/1986 |
| WO | 99/17735 | 4/1999 |

OTHER PUBLICATIONS

Borodkin, S. and Sundberg, D. P., "Polycarboxylic Acid Ion–Exchange Resin Adsorbates for Taste Coverage in Chewable Tablets," *Journal of Pharmaceutical Sciences*, vol. 60, No. 10, Oct. 1971, pp. 1523–1527.
International Search Report dated Mar. 23, 2001.
Block, E., "The Chemistry of Garlic and Onions," *Scientific American Mar.*, 1985, pp. 114–119.
Tarkovskaya, I.A.; Stavitskaya, S.S.; and Tikhonova, L.P., "Sorption and Ion–Exchange Processes: Removal of Sulfur Compounds from Air–Gas Mixtures with Modified Carbon Materials," *Russian Journal of Applied Chemistry*, vol. 69, No. 4, 1996, pp. 543–547.
Ruiz, R.; Hartman, T.G.; Karmas, K.; Lech, J.; and Rosen, R.T., "Breath Analysis of Garlic–Borne Phytochemicals in Human Subjects: Combined Adsorbent Trapping and Short–Path Thermal Desorption Gas Chromatography—Mass Spectrometry," *Food Phytochemicals I: Fruits and Vegetables*, Chapter 7, pp. 102–119.
International Search Report dated Jan. 25, 2001.
Abstract of Lion Corp JPN 2600653B2 Oral Dose of Silicon Gel and Adsorbent for Deodorizing Bad Breath, Apr. 1997.*
Abstract of Japanese Patent No. 54–020,159.
Abstract of French Patent No. 2,141,894.

* cited by examiner

Primary Examiner—Shep K. Rose
(74) Attorney, Agent, or Firm—Ratner Prestia

(57) ABSTRACT

Compositions for adsorbing sulfur-containing compounds and eliminating or reducing odors associated with the ingestion of foods or medicines causing sulfur odor, such as garlic and onions, contain a metal complex of a substrate and a ligand. The complex may be contained in a carrier, such as a silica gel, and has low solubility in an aqueous environment. The ligand of the compositions may comprise an amino acid containing sulfur, nitrogen, or a carboxylic acid, such as cystine, and the substrate is a metal which may be copper, zinc, or iron.

4 Claims, No Drawings

SULFUR ADSORBENT FOR REDUCING ONION OR GARLIC BREATH ODOR

CROSS-REFERENCE TO RELATED APPLICATION

This application claims priority of U.S. Provisional Application No. 60/149,031, filed on Aug. 16, 1999.

TECHNICAL FIELD

The present invention relates generally to compositions and methods for eliminating or reducing breath odors caused by sulfur-containing compounds produced when food products and medicines are ingested. More particularly, it relates to eliminating or reducing breath odors by adsorbing sulfur-containing compounds and their constituents and derivatives contained in foods composed of garlic or onions.

BACKGROUND OF THE INVENTION

Many chemicals and food products contain sulfur-containing compounds, which possess a strong odor. Ingestion of the chemical or food product often results in breath having undesirable odors from either the ingested compounds, from their metabolites, or both. Garlic and onions are foods with particularly strong sulfur odors and cause particularly undesirable breath odors.

Garlic and other food products and chemicals comprise or produce various sulfur-containing constituents, including allicin, alliin, and diallyl disulfide. The sulfur-containing compounds that have been found to result from ingestion of garlic or other food products and chemicals include allyl mercaptan, diallyl disulfide, dimethyl disulfide, dipropyl disulfide, methyl allyl disulfide, allyl methyl sulfide, diallyl sulfide, dimethyl trisulfide, methyl allyl trisulfide, and allyl thiol.

The elimination of sulfur odor, including odor from foods such as garlic and onions, and from medicines has been attempted using various chemical compounds and processes. Many of these attempts involved removing odor from the breath of an individual.

It has been reported that both chlorophyll and lemon juice will eliminate the odor associated with consumption of garlic. Further, a combination of cardamom seeds, menthol, coriander, essential oils, and chlorophylls has been used to prevent bad breath. Green tea flavonoid and cyclodextrin have both been used to freshen breath. In addition, cyclodextrin has been used to deodorize garlic extracts. Corrinoids also have been used to prevent sulfur odor in certain pharmaceuticals.

Attempts to obtain an odor-free garlic have included treating with ethanol and alpha enzyme; dried egg yolk and egg shell; myo-inositol hexaphosphate ester, egg powder, or both; magnesium hydroxide; a suspension of calcium (and/or magnesium) salt, alginate, zeolite, and diatomaceous earth; sodium bicarbonate and a mixture of organic acids; alpha and beta unsaturated organic acids; minced pork meat and powdered carrot leaves; silica gel, phytic acid, and zinc salts; carbonate and acetic acid; a solution of sweet sake, vinegar, citric acid, and egg whites; Vitamin C and various dried plant parts; magnesium oxide powder; and drying by heating in a carbon dioxide atmosphere. A common problem with many of these compositions and methods is that they alter the flavor of foods or orally ingested medicines when incorporated into those foods or medicines.

Additionally, sulfur adsorbents have generally been used for removal of sulfur dioxide, instead of reduced forms of sulfur, such as hydrogen sulfide, mercaptans, and allyl sulfides, which are commonly found in garlic and its derivatives. Generally, the previously used compounds include carbon and copper, copper oxides, copper carbonate on cellulose, clinoptilolite, and copper supported on aluminum silicate. These have not been incorporated into food.

Therefore, a need still exists for compositions and processes for adsorbing sulfur-containing compounds and eliminating or reducing sulfur odors, such as those found in garlic and onions and their derivatives and metabolites, which can be incorporated into foods and orally ingested medicines. To overcome the shortcomings of the conventional adsorbents and treatments to eliminate sulfur-based odors, new sulfur adsorbent compositions and methods for eliminating or reducing sulfur odors from breath are provided.

SUMMARY OF THE INVENTION

To achieve these and other objects, the present invention provides compositions for adsorbing sulfur-containing compounds to eliminate or reduce breath odors caused by garlic, onions, and other foods or medicines. These compositions may be provided in various forms, such as gum, spray, mint, or mouthwash, without hindering their flavor. These compositions are metal complexes having low solubility in an aqueous environment, comprising a substrate and a ligand and, optionally, a support. The ligand may comprise an amino acid whose side chain contains sulfur, nitrogen, or a carboxylic acid; the substrate may comprise a metal which complexes with the ligand. Optionally, the complex is contained in a carrier. In addition, a polystyrene-based strong cation exchanger complexed to a metal ion functions as a sulfur compound adsorbent.

In a further embodiment of the present invention, the complex comprises a naturally occurring amino acid, a modified naturally occurring amino acid, or a non-naturally occurring amino acid, each of whose side chain contains sulfur, nitrogen, or a carboxylic acid, and a complexing metal. The complex is substantially insoluble in water or other aqueous environment and is distributed throughout a silica gel. The gel carrier having the complex distributed throughout is less soluble in an aqueous environment than the complex itself.

In yet another embodiment of the present invention, methods for eliminating or reducing sulfur odors associated with the consumption of foods, such as garlic and onions, or medicines are provided. These methods comprise orally administering the sulfur adsorbent compositions of the present invention to an individual who has consumed a food or medicine that generates sulfur odors.

It is to be understood that both the foregoing general description and the following detailed description are exemplary, but are not restrictive, of the invention.

DETAILED DESCRIPTION OF THE INVENTION

The sulfur adsorbent compositions of the present invention comprise a complex of two components: a substrate and a ligand. The ligand is generally an amino acid and the substrate is a metal which complexes with the ligand. The components of the adsorbent compositions preferably have low solubility in water and are contained in a carrier. The low solubility of the complex allows for the adsorbent to be present longer at the site of adsorption, such as in the mouth.

The amino acid may be one whose side chain contains sulfur, such as cysteine or methionine; one whose side chain contains nitrogen, such as tryptophan, asparagine, glutamine, lysine, arginine, or histidine; or one whose side chain is a carboxylic acid, such aspartic acid, or glutamic acid. Both the naturally occurring form and a modified form of the amino acid may be used in the complex. Further, a non-naturally occurring amino acid whose side chain contains sulfur, nitrogen, or a carboxylic acid may be incorporated into the complex. For example, a non-naturally occurring amino acid, similar to cysteine, but with the methyl group of the $CH_2$—SH side chain replaced with a similar alkyl group, such as an ethyl or propyl group, may be used.

A modified form of the amino acids contemplate minor changes to the amino acid not resulting in any substantial change in functionality. Oxidation is one type of modification that may be made to a naturally occurring amino acid. Cysteine may be modified by oxidation to form the diamino acid cystine.

The complexing agent is a metal, preferably, copper, zinc, iron, or any other suitable complexing metal. The carrier may be a gel, such as a silica gel, or any other suitable carrier material. The preferred adsorbent contains a complex of cystine (or cystine HCl) and copper in a silica gel.

The complex has low solubility in water or other aqueous environment. For example, when contacted with saliva, the complex remains a substantially undissolved solid for at least one hour in typical conditions of the human mouth.

The compositions are effective in eliminating or removing breath odors caused by sulfur-containing compounds. Examples of such odors are the odors caused by the substituents and metabolites of garlic. These may consist of allyl sulfides such as allicin and The compositions may be in the form of a powder that allows their incorporation into chewing gum, mints, or other products, or in an alternative solid or liquid form, such as a mouthwash or a spray. The compositions do not affect the flavors of gum or other products in which they are incorporated. Specifically, the sulfur adsorbent compositions of the present invention do not affect the aroma of mint oil that is often present in chewing gum, mint formulations, or mouthwashes.

A metal complex with a material other than an amino acid can also be an effective sulfur odor-reducing composition. A compound having a strong cation exchanger as a functional group, such as sulfonic acid, may be complexed to a metal ion to form a complex active in removing odors from sulfur-containing compounds. As used herein, the phrase "strong cation exchanger" has its conventional meaning, namely a compound which readily undergoes a reversible chemical reaction in which cations are interchanged between it and another compound. One type of strong cation exchanger is a polystyrene-based strong cation exchanger, formed from the monomer $(C_6H_5CHCH_2)_n$, and preferably having an $SO_3^-$ group at the 3' position. For example, the polystyrene-based strong cation exchange resin, Dowex® 50W (from Dow Chemical Company), when complexed with a metal ion, is an effective sulfur adsorbent.

The composition of the present invention is administered by oral placement of the gum, mint, spray, mouthwash, or other vehicle for delivering the composition. Preferably, the composition remains in the mouth for a period of time sufficient to eliminate or reduce the sulfur-associated odor, up to about one hour.

The concentration of the adsorbent in the gum, mint, mouthwash, or spray can vary over a wide range and depend on a number of factors varying with each situation. These factors include the type of the complex, the odors being reduced, the form of the food, and the desired duration of effectiveness. In one example, a cystine-copper was added to gum a concentration of 0.3 wt. %. Also, when a carrier is used, the concentration of the metal complex in the carrier can vary over a wide range. The concentration should not be so high as to adversely affect gelation of the carrier, but not so low as to be ineffective. A concentration of 20 wt. % complex in carrier has been found suitable.

Although reference is made herein to adsorption and adsorbent, this should not be read to exclude other mechanisms occurring to reduce odors. Although it is believed that adsorption is the primary mechanism for reducing odors, other mechanisms, such as absorption, may also occur.

EXAMPLES

Example 1

Synthesis of Cystine-copper Complex

A solution of cystine was made by combining 40 ml of water with 4.42 grams of cysteine HCl and bringing it to a pH of 10 with 1M NaOH. A drop of 1M cupric sulfate was added, and oxygen was bubbled through the solution at room temperature until the purple solution turned green. The pH was adjusted to pH 6–8 using hydrochloric acid.

A solution of the metal salt was made by combining 4.32 g of cupric chloride dihydrate with 10 ml water. The insoluble complex formed instantly when the metal and amino acid solutions were slowly combined with stirring. The pH was adjusted to pH 6–8 using 1M sodium hydroxide. The complex was washed with water and removed by filtration in a Buechner funnel. The complex was dried overnight in an oven at 60° C.

Example 2

Synthesis of silica-supported cystine-copper complex An aqueous suspension (5 g in 50 ml) of the cystine-copper complex of Example 1 was mixed with diluted sodium silicate (200 ml of sodium silicate (3:22 ratio of $SiO_2:Na_2O$ w/w, 37.6% solids)+200 ml water), to which about 20 ml of 8N sulfuric acid was rapidly added and mixed. The suspension gelled within 3 minutes. After 60 minutes of incubation at room temperature, the solid was then crushed, washed with water to a conductivity of 650 µSeimens, dried at 60° C., and then milled to a powder.

Example 3

Synthesis of Polystyrene-based Cation Exchanger-copper Complex

An aliquot (2.0 g) of Dowex® 50W ($H^+$ form, 200–400 mesh) was stirred at room temperature for 2 minutes with 50 ml of 0.1 M cupric chloride. The pH was adjusted to neutrality with 10N and 1N sodium hydroxide, and string continued for 10 more minutes. The green solid was then filtered, washed 3 times with 500 ml of water, and dried overnight at 60° C.

Example 4

Activity of Cystine-copper Complex

All dilution operations were done using water under nitrogen in capped bottles. Hydrogen sulfide was measured as a gas in a syringe and injected into a sealed bottle containing deoxygenated water. The concentration (ppb w/w) was calculated assuming all of the hydrogen sulfide ($H_2S$) dissolved in the water after shaking, and using the density of the gas.

All of the liquid compounds were handled by syringe. Concentrations of thiols are reported assuming that their specific gravity is 1. Adsorbents, as made by Example 1, were weighed as dry powders into bottles before sealing and before the addition of room temperature dilute sulfide solution. After 20 minutes of shaking, the bottle was unsealed and the contents carefully sniffed.

Table 1 shows the adsorption of sulfur compounds even in the presence of mint oil. The object of the experiment was to remove the thiol odor but not to remove the mint oil aroma. Not only did the adsorbent remove the odor of all three sulfur compounds, but it did not reduce the aroma of the mint oil at all.

TABLE 1

Sulfur compound adsorption in the presence of mint oil. All sulfur compounds were present at 5 ppb (w/v) except hydrogen sulfide (50 ppb). Mint oil was added to the 50 ppb level. Adsorbent was at 0.1% w/v.

| Sulfur compound | $H_2S$ | | Diallyl disulfide | | Propane thiol | | Allyl Mercaptan | |
|---|---|---|---|---|---|---|---|---|
| Smell | Garlic | Mint | Garlic | Mint | Garlic | Mint | Garlic | Mint |
| Effect | None | strong | v. weak | OK | Faint | OK | v. faint | OK |

Example 5
Activity of other Metal-amino Acid Complexes

Each amino acid solution was made by dissolving 2.74 g of the amino acid into 40 ml of water. The complex with the metal was synthesized as described in the second step of Example 1.

Odor removal was tested using 5 ml of a solution containing 627 nmol of allyl mercaptan in water. A suspension of the metal complex was mixed with the mercaptan solution, reacted in a sealed vial for 10 minutes at room temperature, and then sniffed for residual odor.

Table 2 shows that in addition to copper complexes, ferric iron and zinc

TABLE 2

Activity of metal complexes in removing garlic odor.

| Amino Acid Metal | Meth-ionine | Aspar-agine | Cys-teine | Cys-tine | Gly-cine | Aspartic Acid | Ion Exch. Resin (Dowex 50) |
|---|---|---|---|---|---|---|---|
| Cu | ? | ++ | ++ | ++ | – | ++ | + |
| Fe III | ? | + | + | + | – | + | + |
| Zn | ? | + | + | + | – | + | + |
| Mg | – | – | – | – | – | – | – |
| Mn | – | – | NA | NA | – | – | + |

Key:
++ = complete odor removal; + = slight odor remaining; – = no odor removal; NA = complex was not insoluble; ? = allyl mercaptan smell masked by methionine smell.

As indicated above and shown in Table 2, a metal complex with a material other than an amino acid is effective. A compound having a strong cation exchanger as a functional group, such as sulfonic acid, may be completed to a metal ion to form a complex active in removing odors from sulfur-containing compounds. For example, the polystyrene-based strong cation exchange resin, Dowex® 50 (38–75 $\mu$m in particle size, and obtained from Dow Chemical Company), when complexed with a metal ion, is an effective sulfur adsorbent.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A composition for adsorbing sulfur comprising a complex of cystine HCl and copper in a carrier comprising silica gel and having a low solubility in an aqueous environment.

2. The composition of claim 1, wherein said complex is present in said carrier at a concentration of 20 wt. %.

3. A composition for adsorbing sulfur consisting essentially of a complex of cystine HCl and copper in a carrier comprising silica gel and having a low solubility in an aqueous environment.

4. The composition of claim 3, wherein said complex is present in said carrier at a concentration of 20 wt. %.

* * * * *

UNITED STATES PATENT AND TRADEMARK OFFICE
CERTIFICATE OF CORRECTION

PATENT NO. : 6,403,642 B1
DATED : June 11, 2002
INVENTOR(S) : Kenneth A. Berg

It is certified that error appears in the above-identified patent and that said Letters Patent is hereby corrected as shown below:

<u>Title page,</u>
Item [56], References Cited, U.S. PATENT DOCUMENTS, insert the following:
-- 5,897,891    4/1999      Godfrey ..................................... 426/74
4,863,898    9/1989      Ashmead ................................. 514/6
4,830,716    5/1989      Ashmead ................................. 204/72
4,758,439    7/1988      Godfrey ..................................... 426/74
4,684,528    8/1987      Godfrey ..................................... 426/74
4,816,238    3/1989      Jeffrey ....................................... 423/226
5,833,955    11/1998     Kleinberg et al. ........................... 424/49
5,833,952    11/1998     Grigor et al. ................................ 424/49
4,992,259    2/1991      Schiraldi et al. ............................ 424/49
4,885,156    12/1989     Kotilainen et al. .......................... 424/56
4,425,325    1/1984      Ritchey et al. .............................. 424/54 --

Signed and Sealed this

Eighth Day of April, 2003

JAMES E. ROGAN
*Director of the United States Patent and Trademark Office*